(12) United States Patent
MacDonald

(10) Patent No.: US 7,539,545 B2
(45) Date of Patent: *May 26, 2009

(54) ELECTROMAGNETIC INTERFERENCE IMMUNE PACING/DEFIBRILLATION LEAD

(75) Inventor: Stuart G. MacDonald, Pultneyville, NY (US)

(73) Assignee: Medtronic, Inc., Minneapolis, MN (US)

( * ) Notice: Subject to any disclaimer, the term of this patent is extended or adjusted under 35 U.S.C. 154(b) by 272 days.

This patent is subject to a terminal disclaimer.

(21) Appl. No.: 11/140,071

(22) Filed: May 27, 2005

(65) Prior Publication Data

US 2006/0271146 A1    Nov. 30, 2006

(51) Int. Cl.
*A61N 1/05* (2006.01)

(52) U.S. Cl. .................................. 607/119

(58) Field of Classification Search ............. 174/32–34, 174/36, 103–104, 107–109; 607/115–153; 604/410–412; 156/51–56
See application file for complete search history.

(56) References Cited

U.S. PATENT DOCUMENTS

| | | | | |
|---|---|---|---|---|
| 4,738,734 | A * | 4/1988 | Ziemek ................. | 156/53 |
| 4,841,259 | A * | 6/1989 | Mayer ................. | 333/17.2 |
| 4,926,862 | A | 5/1990 | Miyajima et al. | |
| 5,317,665 | A * | 5/1994 | Herrebrugh ............. | 385/101 |
| 5,433,732 | A | 7/1995 | Hirschberg et al. | |
| 5,490,035 | A | 2/1996 | Yen et al. | |
| 5,496,359 | A * | 3/1996 | Davidson ............... | 607/115 |
| 5,917,157 | A | 6/1999 | Remsburg | |
| 6,184,324 | B1 | 2/2001 | Benz et al. | |
| 6,187,028 | B1 | 2/2001 | Munshi | |
| 6,426,861 | B1 | 7/2002 | Munshi | |
| 6,451,947 | B1 | 9/2002 | Benz et al. | |
| 6,514,276 | B2 | 2/2003 | Munshi | |
| 6,795,730 | B2 | 9/2004 | Connelly et al. | |
| 6,875,180 | B2 | 4/2005 | Weiner et al. | |
| 2001/0011183 | A1 | 8/2001 | Munshi | |
| 2002/0082673 | A1 * | 6/2002 | Benz et al. ............... | 607/116 |
| 2003/0120197 | A1 * | 6/2003 | Kaneko et al. ............ | 604/21 |
| 2003/0176893 | A1 | 9/2003 | Munshi | |
| 2003/0204217 | A1 | 10/2003 | Greatbatch | |
| 2004/0199069 | A1 * | 10/2004 | Connelly et al. .......... | 600/412 |
| 2005/0222642 | A1 | 10/2005 | Przybyszewski et al. | |
| 2005/0222647 | A1 | 10/2005 | Wahlstrand et al. | |

(Continued)

*Primary Examiner*—Carl H Layno
*Assistant Examiner*—Jessica Reidel
(74) *Attorney, Agent, or Firm*—Stephen W. Bauer; Michael J. Ostrom

(57) ABSTRACT

An electromagnetic interference immune defibrillator lead has a first electromagnetic insulating layer. A first layer is formed on the first electromagnetic insulating layer, the first layer having a plurality of first conductive rings composed of first conductive material, each first conductive ring being separated by first insulating material. A second electromagnetic insulating layer is formed on the first layer. A second layer is, formed on the second electromagnetic insulating layer, the second layer having a plurality of second conductive rings composed of second conductive material, each second conductive ring being separated by second insulating material. A third electromagnetic insulating layer is formed on the second layer. The second conductive rings of second conductive material are positioned such that a second conductive ring overlaps a portion of a first conductive ring and overlaps a portion of a second conductive ring, the second conductive ring being adjacent to the first conductive ring. The second electromagnetically insulating layer is composed of a self-healing dielectric material.

10 Claims, 14 Drawing Sheets

U.S. PATENT DOCUMENTS

2005/0222656 A1 10/2005 Wahlstrand et al.
2005/0222657 A1 10/2005 Wahlstrand et al.
2005/0222658 A1 10/2005 Hoegh et al.
2005/0222659 A1 10/2005 Olsen et al.

* cited by examiner

ELECTROMAGNETIC INTERFERENCE IMMUNE PACING/DEFIBRILLATION LEAD

FIELD OF THE PRESENT INVENTION

The present invention relates to electromagnetic interference immune pacing/defibrillation leads. More specifically, the present invention pertains to the use of dielectric materials with defibrillation leads which enables a conductive path for defibrillation pulses and is immune to electromagnetic interference induced voltages.

BACKGROUND OF THE PRESENT INVENTION

Magnetic resonance imaging has been developed as an imaging technique adapted to obtain both images of anatomical features of human patients as well as some aspects of the functional activities of biological tissue. These images have medical diagnostic value in determining the state of the health of the tissue examined.

In a magnetic resonance imaging process, a patient is typically aligned to place the portion of the patient's anatomy to be examined in the imaging volume of the magnetic resonance imaging apparatus. Such a magnetic resonance imaging apparatus typically comprises a primary magnet for supplying a constant magnetic field ($B_0$) which, by convention, is along the z-axis and is substantially homogeneous over the imaging volume and secondary magnets that can provide linear magnetic field gradients along each of three principal Cartesian axes in space (generally x, y, and z, or $x_1$, $x_2$ and $x_3$, respectively). A magnetic field gradient ($\Delta B_0/\Delta x_i$) refers to the variation of the field along the direction parallel to $B_0$ with respect to each of the three principal Cartesian axes, $x_i$. The apparatus also comprises one or more RF (radio frequency) coils which provide excitation and detection of the magnetic resonance imaging signal.

The use of the magnetic resonance imaging process with patients who have implanted medical assist devices; such as cardiac assist devices or implanted insulin pumps; often presents problems. As is known to those skilled in the art, implantable devices (such as implantable pulse generators, leads, cardioverters, defibrillators, and/or pacemakers) are sensitive to a variety of forms of electromagnetic interference (EMI) because these enumerated devices include sensing and logic systems that respond to low-level electrical signals emanating from the monitored tissue region of the patient. Since the sensing systems and conductive elements of these implantable devices are responsive to changes in local electromagnetic fields, the implanted devices are vulnerable to external sources of severe electromagnetic noise, and in particular, to electromagnetic fields emitted during the magnetic resonance imaging procedure. Thus, patients with implantable devices are generally advised not to undergo magnetic resonance imaging procedures.

Continuing with the example of shielding from magnetic resonance imaging interference, it is noted that magnetic resonance imaging procedures are the most widely applied medical imaging modality, with the exception of x-ray procedures. Significant advances occur daily in the magnetic resonance imaging field, expanding the potential for an even broader usage.

There are primarily three sources of voltage that could lead to the malfunction of an implantable device, during a magnetic resonance imaging procedure. First, a static magnetic field is generally applied across the entire patient to align proton spins. Static magnetic field strengths up to 7 Tesla for whole body human imaging are now in use for research purposes. The increase in field strength is directly proportional to the acquired signal to noise ratio (SNR) which results in enhanced magnetic resonance image resolution. Consequently, there is impetus to increase static field strengths, but with caution for patient safety. These higher field strengths are to be considered in the development of implantable devices.

It is noted that for image acquisition and determination of spatial coordinates, time-varying gradient magnetic fields of minimal strength are applied in comparison to the static field. The effects of the gradients are seen in their cycling of direction and polarity. With present day pulse sequence design and advances in magnetic resonance imaging hardware, it is not uncommon to reach magnetic gradient switching speeds of up to 50 Tesla/sec (this is for clinical procedures being used presently). Additionally, fast imaging techniques such as echo-planar imaging and turbo FLASH are in use more frequently in the clinic. Non-invasive magnetic resonance angiography uses rapid techniques almost exclusively on patients with cardiovascular disease.

Previous research evaluating the effects of magnetic resonance imaging on pacemaker function did not include these fast techniques. Therefore, the use of magnetic resonance imaging for clinical evaluation for individuals with implantable cardiac devices may be an issue of even greater significance. Rapid magnetic resonance imaging techniques use ultra-fast gradient magnetic fields. The polarities of these fields are switched at very high frequencies. This switching may damage implantable devices or cause them to malfunction.

Lastly, in magnetic resonance imaging, a pulsed RF field is applied for spatial selection of the aligned spins in a specimen during a magnetic resonance imaging procedure. USFDA regulations relative to the power limits of the RF fields are in terms of a specific absorption rate (SAR), which is generally expressed in units of watts per kilogram. These limits may not consider the effects on implantable devices, as the deleterious effects of transmission of RF fields in the magnetic resonance imaging system may no longer be the primary concern in their design parameters.

It is noted that an implanted device; such as a cardioverter, defibrillator, and/or pacemaker; is used to sustain a patient's life through the regulation of cardiac function. Hence, such patients would be barred from safely availing themselves of magnetic resonance imaging as a diagnostic tool unless their implanted device is effectively shielded from the strongest interference that could be expected from a conventional magnetic resonance imaging session.

Of particular concern is the interaction between a conventional magnetic resonance imaging session and leads that are utilized by the implantable devices. These leads can function as antenna and convey the voltage from the conventional magnetic resonance imaging session to the implanted device or to the tissue of the patient. In one instance, the implantable device may be damaged, thereby jeopardizing the ability to sustain the life of the patient. In the other instance, the tissue of the patient may be seriously injured by the conveyed voltage.

It has been proposed to utilize filters in the leads to block the damaging voltage from being conveyed along the lead. Such filters may contain inductors and capacitors. However, these filters can also interfere with the desired signals being communicated along the leads to and from the implantable device and the tissue region of interest.

For example, a filter on a defibrillator lead must be able to block the damaging voltage from the magnetic resonance imaging session, but also be able to provide a viable path for a large voltage pulse to defibrillate a patient's heart. Conventional filter leads have not reliably provided the desired blocking power of the damaging voltage from the magnetic resonance imaging session and still consistently provide a viable path for a large voltage pulse to defibrillate a patient's heart because these components breakdown after the first defibrillation pulse, thereby destroying the ability to block the damaging voltage from the magnetic resonance imaging session.

Therefore, it is desirable to provide a defibrillator lead that blocks the damaging voltage from the magnetic resonance imaging session. Moreover, it is desirable to provide a defibrillator lead that blocks the damaging voltage from the magnetic resonance imaging session and provides a viable path for a large voltage pulse to defibrillate a patient's heart.

SUMMARY OF THE PRESENT INVENTION

A first aspect of the present invention is an electromagnetic interference immune pacing/defibrillation lead. The electromagnetic interference immune pacing/defibrillation lead includes a pacing lead; a first electromagnetic insulating layer formed around the pacing lead; a first layer formed on the first electromagnetic insulating layer, the first layer having a plurality of first conductive rings composed of first conductive material, each first conductive ring being separated by first insulating material; a second electromagnetic insulating layer formed on the first layer; a second layer formed on the second electromagnetic insulating layer, the second layer having a plurality of second conductive rings composed of second conductive material, each second conductive ring being separated by second insulating material; and a third electromagnetic insulating layer formed on the second layer. The second conductive rings of second conductive material are positioned such that a second conductive ring overlaps a portion of a first conductive ring and overlaps a portion of an adjacent first conductive ring.

A second aspect of the present invention is an electromagnetic interference immune pacing/defibrillation lead. The electromagnetic interference immune pacing/defibrillation lead includes a pacing lead; a first electromagnetic insulating layer formed around the pacing lead; a first layer, formed on the first electromagnetic insulating layer, the first layer having a plurality of first conductive rings composed of first conductive material, each first conductive ring being separated by first insulating material; a second electromagnetic insulating layer formed on the first layer; a second layer, formed on the second electromagnetic insulating layer, the second layer having a spiraling coil of loops, the spiraling coil being composed of second conductive material, each loop being separated by second insulating material; and a third electromagnetic insulating layer formed on the second layer. The spiraling coil of loops is positioned such that a section of the spiraling coil of loops ring overlaps a portion of a first conductive ring and overlaps a portion of an adjacent first conductive ring.

A third aspect of the present invention is an electromagnetic interference immune defibrillation lead. The electromagnetic interference immune defibrillation lead includes a first electromagnetic insulating layer; a first layer, formed on the first electromagnetic insulating layer, the first layer having a plurality of first conductive rings composed of first conductive material, each first conductive ring being separated by first insulating material; a second electromagnetic insulating layer formed on the first layer; a second layer, formed on the second electromagnetic insulating layer, the second layer having a plurality of second conductive rings composed of second conductive material, each second conductive ring being separated by second insulating material; and a third electromagnetic insulating layer formed on the second layer. The second conductive rings of second conductive material are positioned such that a second conductive ring overlaps a portion of a first conductive ring and overlaps a portion of an adjacent first conductive ring.

A fourth aspect of the present invention is an electromagnetic interference immune defibrillation lead. The electromagnetic interference immune defibrillation lead includes a first electromagnetic insulating layer; a first layer, formed on the first electromagnetic insulating layer, the first layer having a plurality of first conductive rings composed of first conductive material, each first conductive ring being separated by first insulating material; a second electromagnetic insulating layer formed on the first layer; a second layer, formed on the second electromagnetic insulating layer, the second layer having a spiraling coil of loops, the spiraling coil being composed of second conductive material, each loop being separated by second insulating material; and a third electromagnetic insulating layer formed on the second layer. The spiraling coil of loops is positioned such that a section of the spiraling coil of loops ring overlaps a portion of a first conductive ring and overlaps a portion of an adjacent first conductive ring.

A fifth aspect of the present invention is a method of forming an electromagnetic interference immune defibrillation lead. The method provides a first electromagnetic insulating layer; forms metalized strips on the first electromagnetic insulating layer; provides a second electromagnetic insulating layer; forms metalized strips on the second electromagnetic insulating layer; provides a third electromagnetic insulating layer; and fuses the first, second, and third electromagnetic insulating layers together such that the metalized strips on the first electromagnetic insulating layer contact the third electromagnetic insulating layer and the metalized strips on the second electromagnetic insulating layer contact the third electromagnetic insulating layer.

A sixth aspect of the present invention is a method of constructing an electromagnetic interference immune pacing/defibrillator lead. The method provides a pacing lead; wraps a first tape, spirally, around the pacing lead, the first tape being composed of a first insulating substrate with conductive strips formed thereon, the first tape being wrapped such that the first insulating substrate is adjacent the defibrillator lead, the conductive strips being formed at an angle on the first insulating substrate such that upon wrapping the conductive strips form conductive rings that conduct circumferentially; wraps a second tape, spirally, around the first tape, the second tape being composed of a second insulating substrate; and wraps a third tape, spirally, around the second tape, the third tape being composed of a third insulating substrate with conductive strips formed thereon, the third tape being wrapped such that the conductive strips are adjacent the second tape, the conductive strips being formed at an angle on the third insulating substrate such that upon wrapping the conductive strips form conductive rings that conduct circumferentially.

Another aspect of the present invention is an electromagnetic interference immune implantable medical device. The device includes a selectively conductive structure. The selectively conductive structure includes a first electromagnetic insulating layer; a first layer, formed on the first electromagnetic insulating layer, the first layer having a plurality of first conductive rings composed of first conductive material, each first conductive ring being separated by first insulating material; a second electromagnetic insulating layer formed on the first layer; a second layer, formed on the second electromagnetic insulating layer, the second layer having a plurality of second conductive rings composed of second conductive material, each second conductive ring being separated by second insulating material; and a third electromagnetic insulating layer formed on the second layer. The second conductive rings of second conductive material are positioned such that a second conductive ring overlaps a portion of a first conductive ring and overlaps a portion of an adjacent first conductive ring.

Another aspect of the present invention is an electromagnetic interference immune implantable medical device. The device includes a selectively conductive structure. The selectively conductive structure includes a first electromagnetic insulating layer; a first layer, formed on the first electromagnetic insulating layer, the first layer having a plurality of first conductive rings composed of first conductive material, each first conductive ring being separated by first insulating material; a second electromagnetic insulating layer formed on the first layer; a second layer, formed on the second electromagnetic insulating layer, the second layer having a spiraling coil of loops, the spiraling coil being composed of second conductive material, each loop being separated by second insulating material; and a third electromagnetic insulating layer formed on the second layer. The spiraling coil of loops is positioned such that a section of the spiraling coil of loops ring overlaps a portion of a first conductive ring and overlaps a portion of an adjacent first conductive ring.

Another aspect of the present invention is an electromagnetic interference immune modular defibrillation lead. The lead includes a first conductive modular lead, the first conductive modular lead including a conductive layer insulated by electrically insulating material, the first conductive modular lead including a first interface and a second interface; a capacitor modular component, the capacitor modular component including a capacitor having a self-healing dielectric, the capacitor modular component having a first interface to match the first interface of the first conductive modular lead; and a second conductive modular lead, the second conductive modular lead including a conductive layer insulated by electrically insulating material, the second conductive modular lead including a first interface and a second interface. The second interface of the second conductive modular lead matches the second interface of the capacitor modular component.

A further aspect of the present invention is an electromagnetic interference immune modular defibrillation lead. The lead includes a plurality of conductive modular leads, each conductive modular lead including a conductive layer insulated by electrically insulating material, each first conductive modular lead including a first interface and a second interface; and a plurality of capacitor modular components, each capacitor modular component being connected between two conductive modular leads, each capacitor modular component including a capacitor having a self-healing dielectric, each capacitor modular component having a first interface to match a first interface of a conductive modular lead.

A further aspect of the present invention is an electromagnetic interference immune modular defibrillation lead. The lead includes a plurality of capacitor modular components, each capacitor modular component being connected to adjacent capacitor modular components, each capacitor modular component including a capacitor having a self-healing dielectric, each capacitor modular component having a first interface to match a first interface of an adjacent capacitor modular component.

A further aspect of the present invention is an electromagnetic interference immune modular defibrillation lead. The lead includes a first electromagnetic insulating layer; a first layer, formed on the first electromagnetic insulating layer, the first layer being composed of first conductive material; a second electromagnetic insulating layer formed on the first layer; a second layer, formed on the second electromagnetic insulating layer, the second layer being composed of second conductive material; and a third electromagnetic insulating layer formed on the second layer. A proximal end of the first layer is connected to a voltage source. A distal end of the second layer is connected to an electrode to apply voltage to heart tissue. A distal end of the first layer is electrically insulated. A proximal end of the second layer is electrically insulated.

A further aspect of the present invention is an electromagnetic interference immune modular defibrillation lead. The lead includes a first electromagnetic insulating layer; a first layer, formed on the first electromagnetic insulating layer, the first layer being composed of first conductive material; a second electromagnetic insulating layer formed on the first layer; a second layer, formed on the second electromagnetic insulating layer, the second layer being composed of second conductive material; and a third electromagnetic insulating layer formed on the second layer. A proximal end of the second layer is connected to a voltage source. A distal end of the first layer is connected to an electrode to apply voltage to heart tissue. A distal end of the second layer is electrically insulated. A proximal end of the first layer is electrically insulated.

BRIEF DESCRIPTION OF THE DRAWINGS

The present invention may take form in various components and arrangements of components, and in various steps and arrangements of steps. The drawings are only for purposes of illustrating a preferred embodiment and are not to be construed as limiting the present invention, wherein.

DETAILED DESCRIPTION OF THE DRAWINGS

Figure 1:
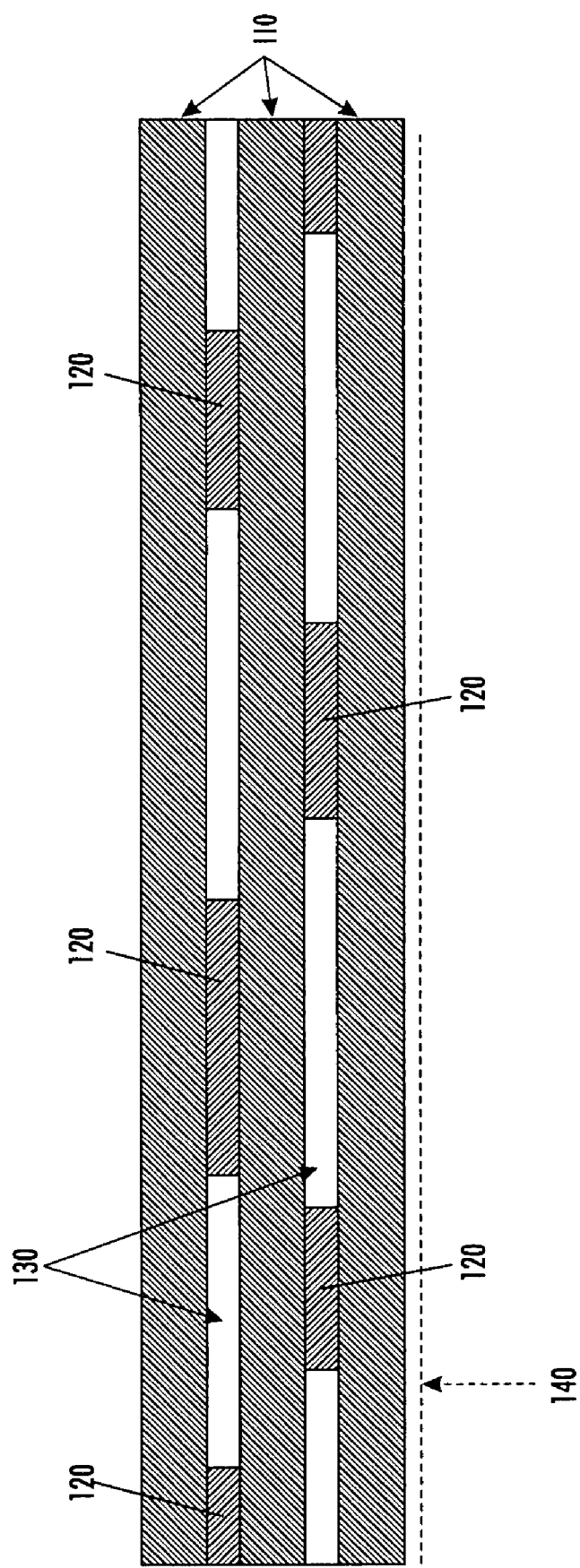
FIG. 1 illustrates an electromagnetic interference immune pacing/defibrillation lead according to the concepts of the present invention.

The present invention will be described in connection with preferred embodiments; however, it will be understood that there is no intent to limit the present invention to the embodiments described herein. On the contrary, the intent is to cover all alternatives, modifications, and equivalents as may be included within the spirit and scope of the present invention, as defined by the appended claims.

For a general understanding of the present invention, reference is made to the drawings. In the drawings, like references have been used throughout to designate identical or equivalent elements. It is also noted that the various drawings illustrating the present invention are not drawn to scale and that certain regions have been purposely drawn disproportionately so that the features and concepts of the present invention could be properly illustrated.

As noted above, it is desirable to provide a defibrillator lead that blocks the damaging voltage from the magnetic resonance imaging session. Moreover, it is desirable to provide a defibrillator lead that blocks the damaging voltage from the magnetic resonance imaging session and provides a viable path for a large voltage pulse to defibrillate a patient's heart.

One solution to providing a defibrillator lead that blocks the damaging voltage from the magnetic resonance imaging session and provides a viable path for a large voltage pulse to defibrillate a patient's heart is to utilize a defibrillation lead having self-healing dielectric properties. Moreover, such a structure should be flexible enough to not constrict the conventional freedom of movement expected in such leads.

Self-healing dielectrics can be explained using the example of a short circuit in a plate capacitor insulated by a dielectric film. The short circuit causes arcing and decomposition of the dielectric film in the path of the arc. Rather than permitting the decomposition to propagate, the hydrogen, carbon dioxide, and water decomposition products locally passivate the adjacent metal film by vaporization or oxidation of the metal. The device is passivated before any significant current can flow into the fault side of the device. The capacitor returns to its operative mode almost instantly. Examples of self-healing dielectric materials are cellulose triacetate and the cyanoresins.

Another example of a self-healing dielectric material is a structure composed of layers of aluminum oxide ($Al_2O_3$). Such a structure is manufactured by anodizing in two separate steps. This process increases dielectric strength by breaking the continuous pore path found in methods that apply only thicker anodic coatings.

Referring now to FIG. 1, an electromagnetic interference immune pacing/defibrillation lead is illustrated. More specifically, FIG. 1 illustrates a cross-section that shows an electromagnetic interference immune defibrillation lead having layers of self-healing dielectric material 110 and patches of electrically conductive material 130 with patches of insulating material 120 therebetween and a pacing wire 140.

The electrically conductive material 130 acts as a block for external electromagnetic interference. When electromagnetic interference induces a charge between the two layers of electrically conductive material 130, the dielectric material 110 prevents a current from arcing between the two layers of electrically conductive material 130 because the voltage level of the current is less than the dielectric threshold of the material.

Conversely, when an intermittent burst of current flows along the defibrillation lead having layers of self-healing dielectric material 110 and patches of electrically conductive material 130, the voltage of that current is not significantly impeded because the voltage level of that current is such that a partial dielectric breakdown occurs in the dielectric material. When the intermittent burst of current is finished, the dielectric material rapidly self-heals and resumes its role in shielding the wire.

In a preferred embodiment, the self-healing dielectric material is cellulose triacetate and the electrically conductive material is copper. It is noted that other self-healing dielectric materials can be used in the present invention, such as aluminum oxide ($Al_2O_3$).

It is noted that the defibrillation lead of FIG. 1 is a plurality of capacitors, self-healing dielectric material 110 between two patches of conductive material 130. The capacitors can be connected in series, parallel, or a combination of both.

If the capacitors, self-healing dielectric material 110 between two patches of conductive material 130, are connected in parallel, the capacitance of each capacitor will add together. The use of a parallel circuit of capacitors, self-healing dielectric material 110 between two patches of conductive material 130, increases the total storage of electric charge. However, the total voltage rating of the capacitors does not change. Every capacitor will "see" the same voltage. Thus, it is preferred that all the capacitors, self-healing dielectric material 110 between two patches of conductive material 130, be rated for the same voltage because the capacitor with lowest voltage rating will govern the breakdown.

On the other hand, if the capacitors, self-healing dielectric material 110 between two patches of conductive material 130, are connected in series, the total capacitance of series connected capacitors will be lower than any one capacitor in the circuit. The use of a parallel circuit of capacitors, self-healing dielectric material 110 between two patches of conductive material 130, offers a higher total voltage rating. In this embodiment, the voltage drop across each capacitor adds up to the total applied voltage. If the capacitors are different, the voltage will divide itself such that smaller capacitors gets more of the voltage because the capacitors get the same charging current, and voltage is inversely proportional to capacitance. Moreover, if one capacitor has a different capacitance, this capacitor will gradually exceed its voltage rating, which will cause an arc through its dielectric barrier and initiating arcing at other capacitors in a cascading fashion.

Figure 2:
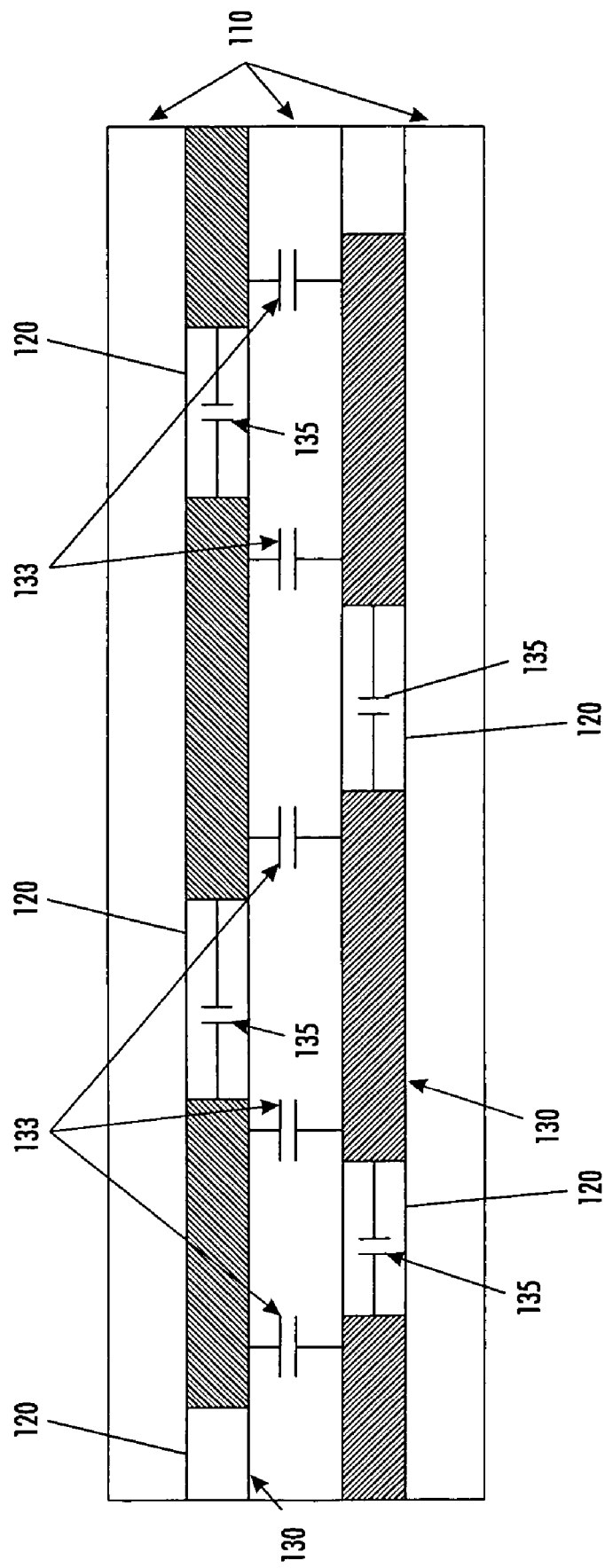
FIG. 2 illustrates a circuit equivalent of the electromagnetic interference immune defibrillation lead of FIG. 1.

As illustrated in FIG. 2, the structure, formed by adjacent, but non-coplanar patches of conductive material 130 and the self-healing dielectric material 110, creates a capacitance, thereby forming a circuit equivalent non-coplanar capacitor 133. Moreover, the structure, formed by adjacent coplanar patches of conductive material 130 and the patch of insulating material 120 therebetween, creates a capacitance, thereby forming a circuit equivalent coplanar capacitor 135.

The insulating material 120 may be chosen for certain dielectric properties in accordance with the desired breakdown properties between adjacent coplanar patches of conductive material 130. Thus, by changing dielectric properties of the insulating material 120, the overall capacitance of the electromagnetic interference immune defibrillation lead can be varied. Moreover, it is noted that the insulating material 120 may also be composed of a self-healing dielectric material such as cellulose triacetate, a cyanoresin, or layered aluminum oxide.

In the above description of FIG. 2, coplanar refers to conductive patches being formed in a same layer or substrate or part of a common wrap or tape, and non-coplanar refers to conductive patches being formed in different layers or substrates or part of different wraps or tapes.

Figure 3:
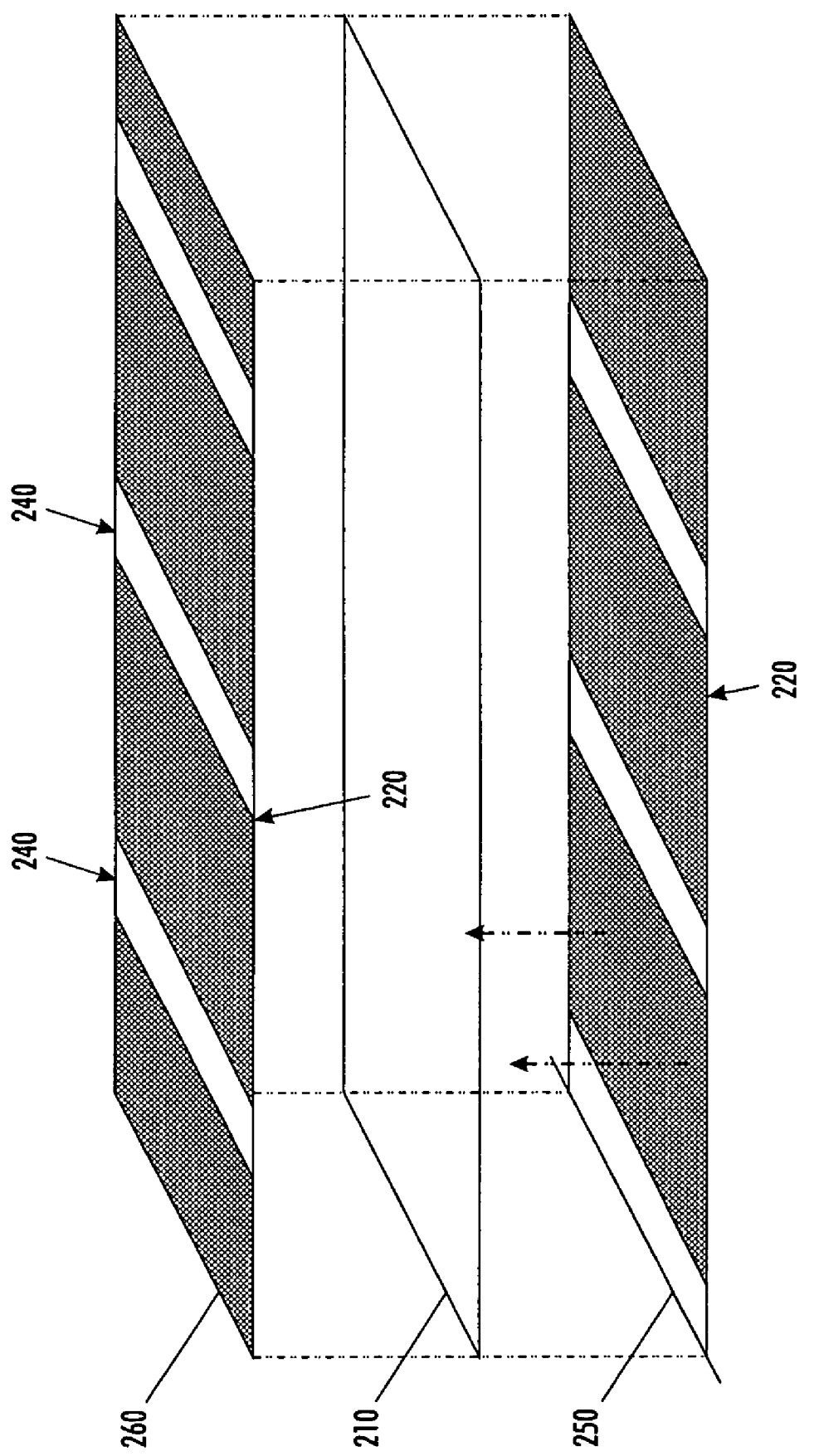
FIG. 3 illustrates a method of forming an electromagnetic interference immune defibrillation lead structure according to the concepts of the present invention.
Figure 4:
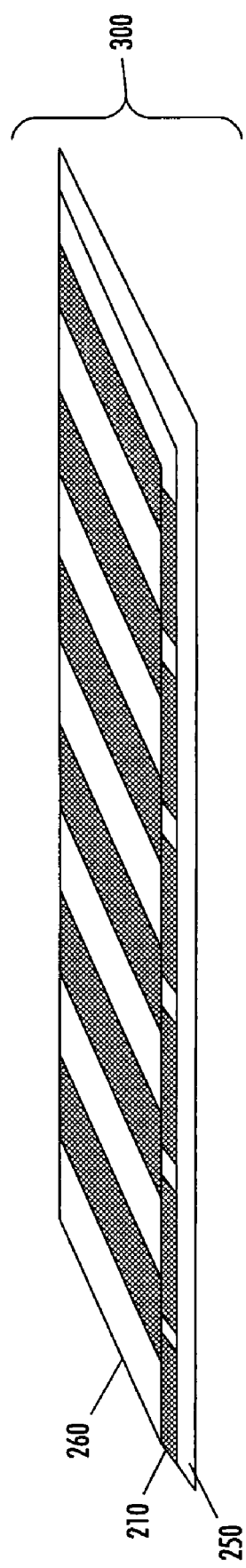
FIG. 4 illustrates the result of the method illustrated in FIG. 3.

As illustrated in FIG. 3, a process for constructing an electromagnetic interference immune defibrillation lead is illustrated. In the illustrated embodiment, a strip of dielectric material 210 is fused between two other strips (250 & 260), each of which is composed of a layer of polymer substrate with alternating patches of conductive material 220 and insulating spaces 240 deposited on one side. The two strips with patches of conductive material (250 & 260) are positioned so that the patches of conductive material 220 of one oppose and face the insulating spaces 240 of the other before fusing the three strips (250, 210, and 260) together. FIG. 4 illustrates an electromagnetic interference immune defibrillation lead substrate 300 resulting from the process of fusing the three strips (260, 210, and 250) together.

Figure 5:
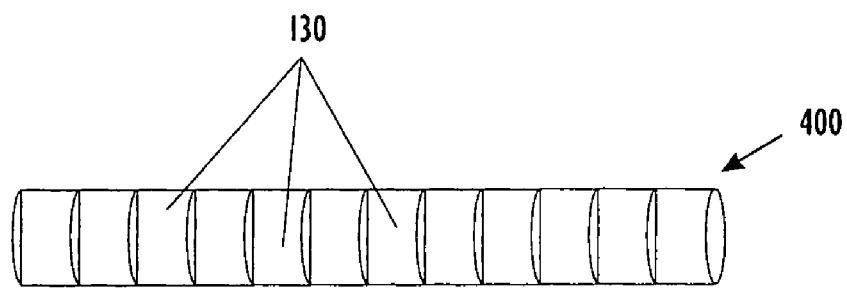
FIG. 5 illustrates an electromagnetic interference immune defibrillation lead according to the concepts of the present invention.

As illustrated in FIG. 5, an electromagnetic interference immune defibrillation lead 400 is constructed using the process illustrated in FIGS. 2 and 3. The electromagnetic interference immune defibrillation lead 400 is formed by rolling electromagnetic interference immune defibrillation lead substrate 300 into a 'C' shaped tube.

Figure 6:
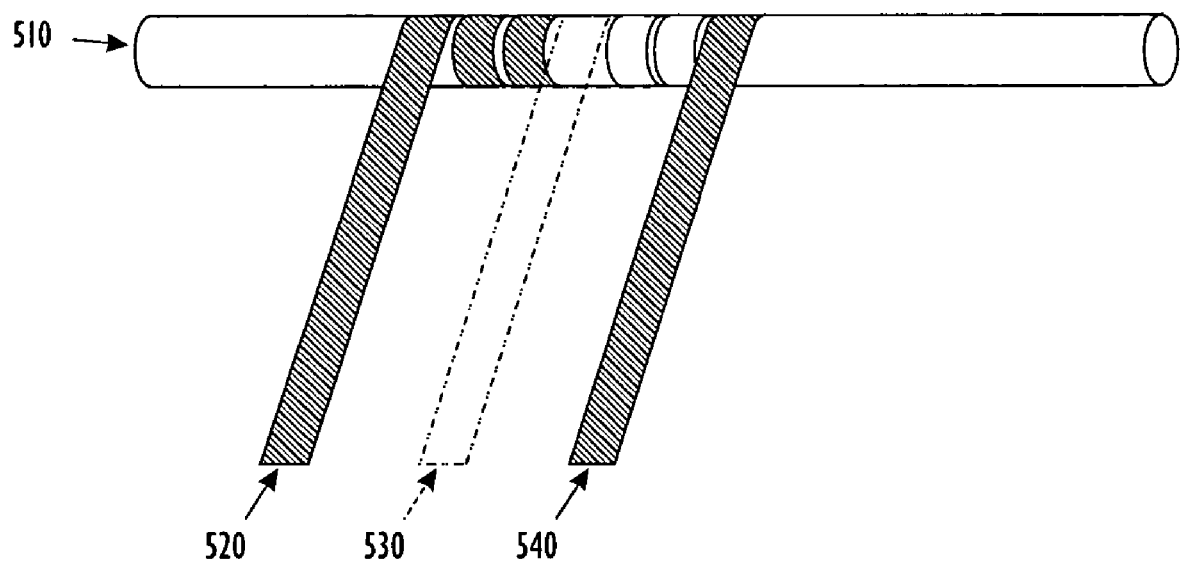
FIG. 6 illustrates the method of constructing an electromagnetic interference immune pacing/defibrillator lead according to the concepts of the present invention.

As illustrated in FIG. 6, a hollow heat-shrink pre-form 510 is wrapped with layers (520, 530, and 540) which layers form an electromagnetic interference immune defibrillation lead. The hollow heat-shrink pre-form 510, so wrapped, results in a heat-shrink assembly.

In a preferred embodiment, this assembly can be applied to an electrically conductive wire.

In another preferred embodiment, this assembly can be applied to a pacing lead. The wire, pacing lead, or any other linear product can be inserted into the wrapped, heat-shrink pre-form 510, which can then be heated causing shrinkage and thus binding to the wire, the pacing lead, or any other linear product.

With respect to FIG. 6, two of the three wraps (520 and 540) are comprised of a self-healing dielectric material coated with an alternating pattern of electrically conductive material and dielectric material. The pattern is comprised of parallel stripes laid down at a predetermined angle with respect to the edge of the particular wrap. The third wrap 530 is comprised of dielectric material only, preferably a self-healing dielectric material.

The diagonally patterned conductive material in two of the three wraps (520 and 540) comes into contact when wrapped around the hollow heat-shrink pre-form to create shielding "rings" that conduct only circumferentially.

In a preferred embodiment, the wrap layers (520, 530, and 540), forming a defibrillation lead, after being applied as described above to a hollow heat-shrink pre-form 510, are finally coated with a conventional biocompatible layer to make the structure suitable for use inside the body of the patient.

In a preferred embodiment, each wrap layer (520, 530, and 540) is about 0.07 millimeters thick, thereby causing an overall increase in outer diameter to be about 0.2 millimeters.

In a preferred embodiment, conventional thermoset materials can be used to coat the structure formed when layers (520, 530, and 540) are wrapped around the hollow heat-shrink pre-form 510, thus creating a solid or firm shell for the defibrillation lead.

Figure 7:
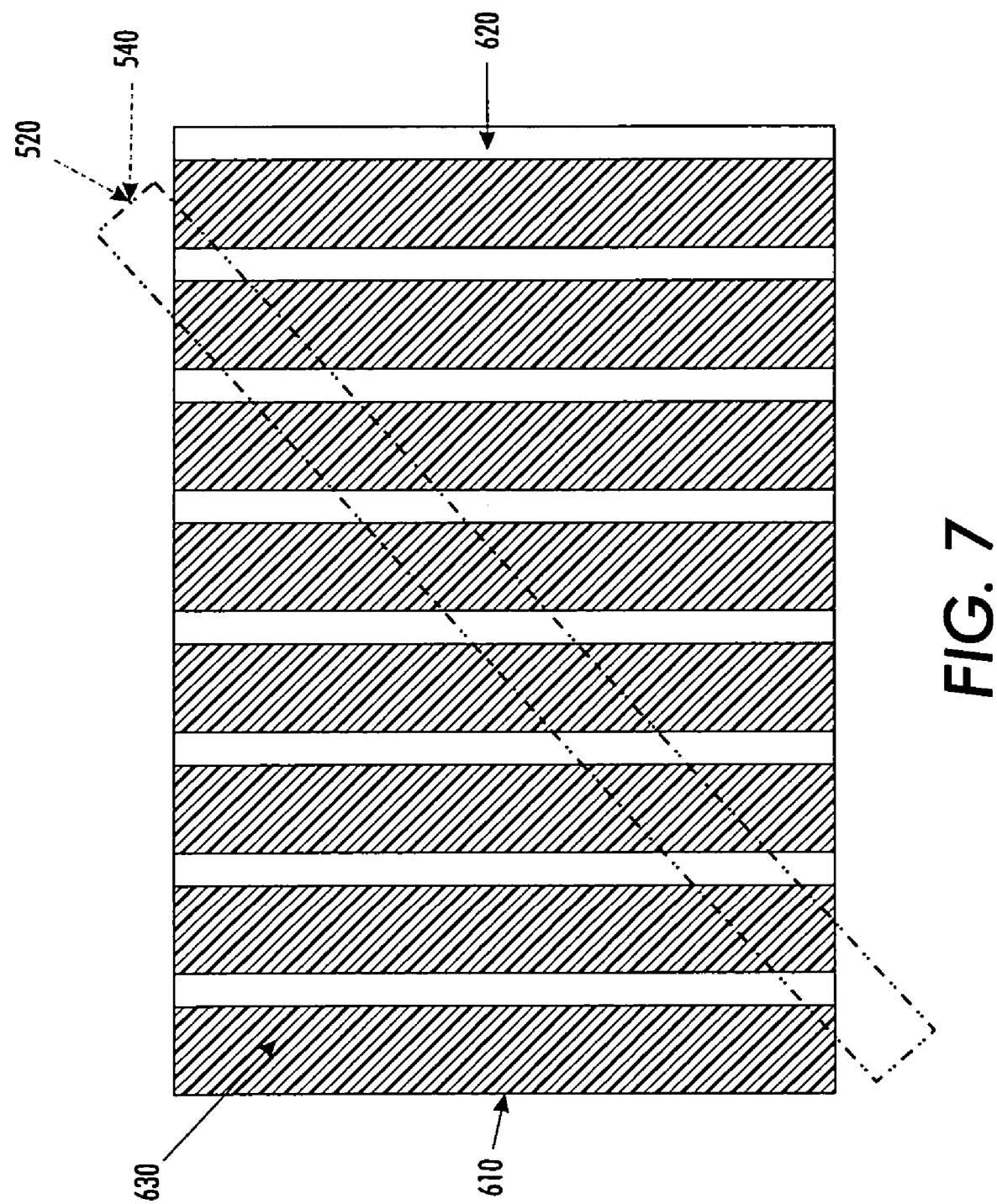
FIG. 7 illustrates a method of making one layer of the electromagnetic interference immune defibrillation lead structure utilized in FIG. 6.

As illustrated in FIG. 7, a primary stock 610, a sheet of alternating electromagnetically insulating material 620 and electrically conductive material 630, is provided. Wraps (520 and 540) are cut from the primary stock 610 at a predetermined angle and a predetermined width.

In a preferred embodiment, the predetermined angle is 45°. The predetermined width can be any width in small enough to allow the electrically conductive pacing wire to undergo the process of wrapping while at the same time being large enough to be processed by a conventional wrapping process as described above.

Figure 8:
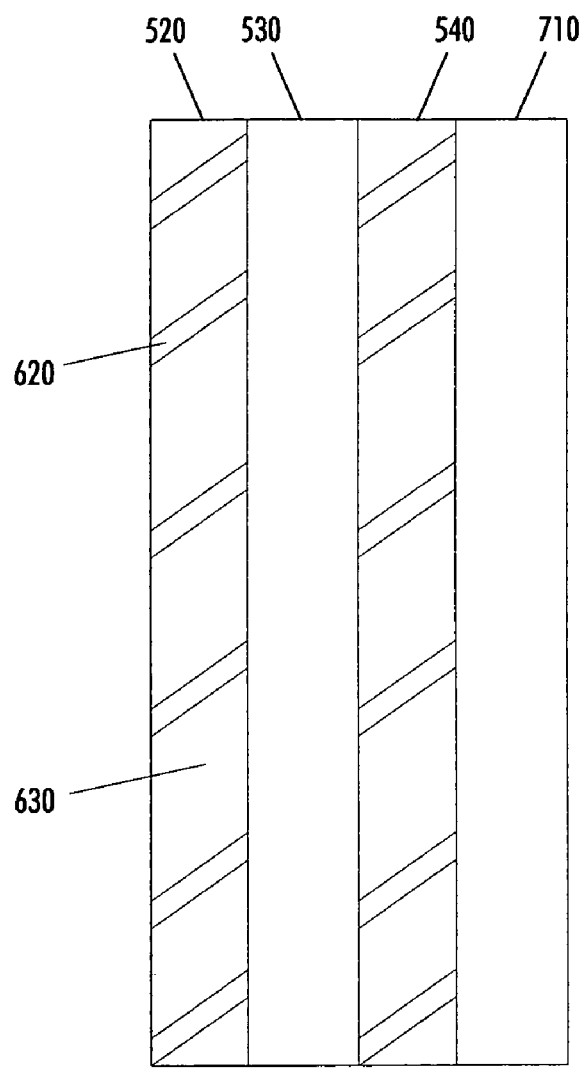
FIG. 8. illustrates another method of forming an electromagnetic interference immune defibrillation lead structure according to the concepts of the present invention.

As illustrated in FIG. 8, four different types of wrapping stock are provided. Each of the four types of wrapping stock is to be applied, in order, to the electrically conductive pacing wire. The order of application is first wrap 520 (having alternating electromagnetically insulating material 620 and electrically conductive material 630), second wrap 530, third wrap 540 (having alternating electromagnetically insulating material and electrically conductive material), and external conventional biocompatible wrap 710. It is noted that the three warps (520, 530, and 540) form an electromagnetic interference immune defibrillation lead.

Figure 9:
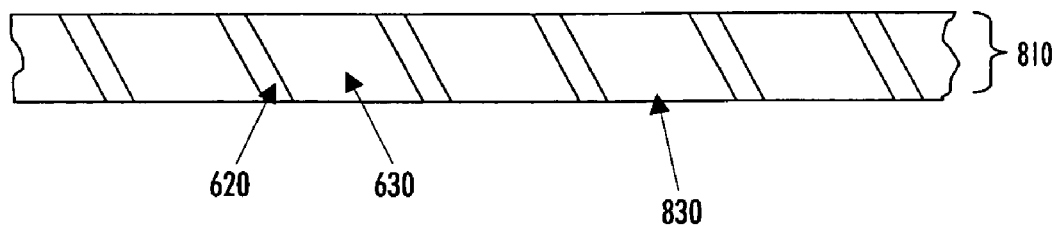
FIG. 9 illustrates an alternate method of making one layer of the electromagnetic interference immune defibrillation lead structure utilized in FIG. 6.

In FIG. 9, a strip 830 with a width 810 equal to an outside diameter needed to surround the electrically conductive pacing wire and a length 820 equal to the length of the pacing wire is cut from primary stock 610. A second strip, not shown in FIG. 9, with the same dimensions as strip 830, is cut from dielectric material only. The second strip is then placed on top of strip 830. Then, another strip, having the same properties of strip 830, is placed on top of the second strip. The three strips are then rolled around the electrically conductive pacing wire forming a complete covering for the pacing wire and heat fused into place.

Figure 10:
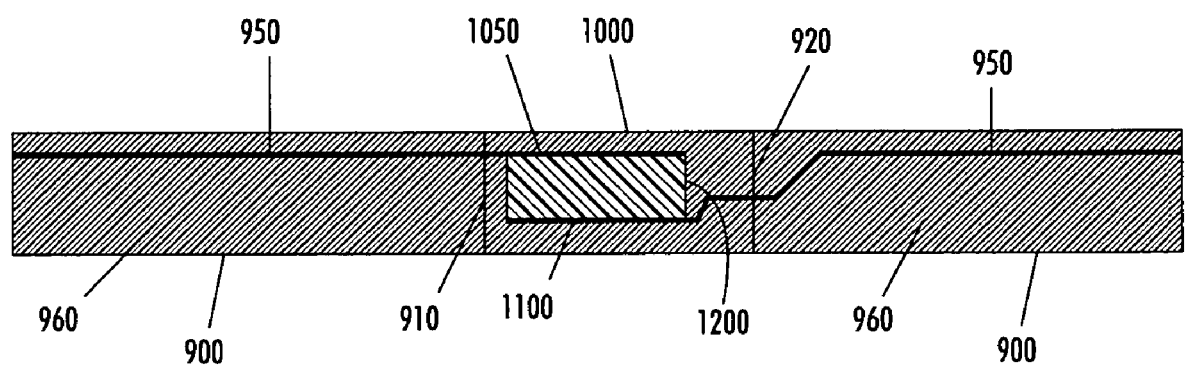
FIG. 10 illustrates a modular electromagnetic interference immune defibrillation lead structure according to the concepts of the present invention.

As illustrated in FIG. 10, an electromagnetic interference immune defibrillation lead can be modularly constructed. In this embodiment, an electromagnetic interference immune defibrillation lead includes a plurality of conductive lead modules 900 connected together by a capacitor module 1000. Each conductive lead module 900 includes a conductor or conductive layer 950 that is insulated by insulating material 960.

Figure 11:
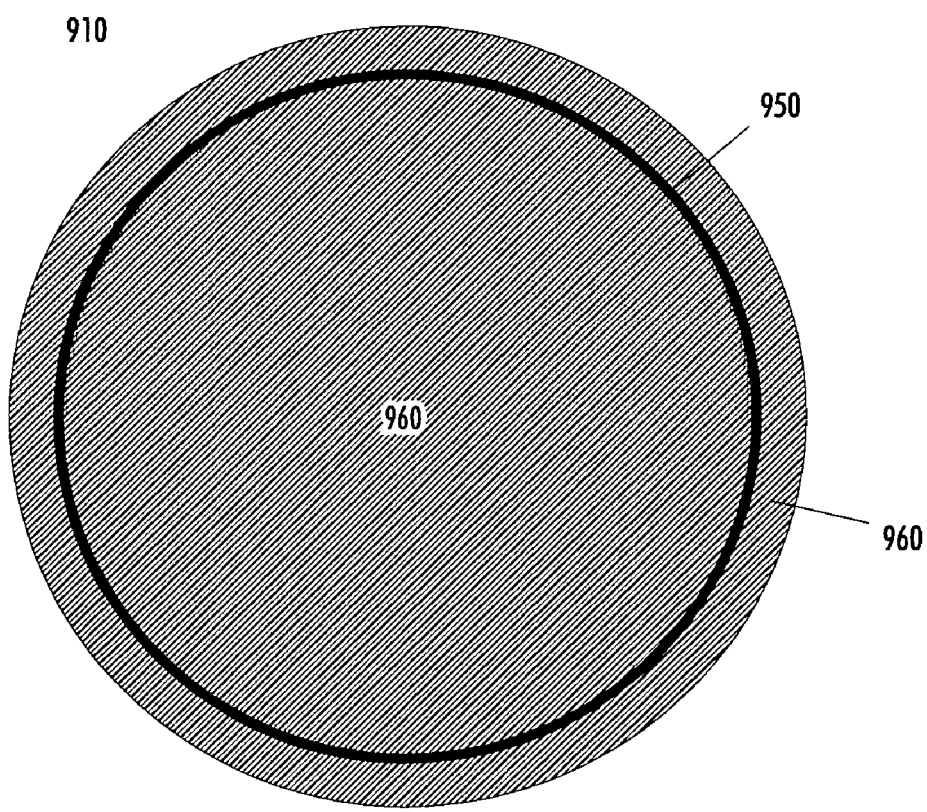
FIG. 11 illustrates a connection configuration for one end of the modular electromagnetic interference immune defibrillation lead structure, as illustrated in FIG. 10, according to the concepts of the present invention.

At one end 910 of a conductive lead module 900, the conductor or conductive layer 950 is positioned at an outer boundary of the electromagnetic interference immune defibrillation lead. The positioning of the conductor or conductive layer 950 at an outer boundary of the electromagnetic interference immune defibrillation lead allows the end 910 of the conductive lead module 900 to connect properly with the appropriate end of capacitor module 1000. FIG. 11 provides a cross-section view of end 910 of the conductive lead module 900.

As illustrated in FIG. 11, the end 910 of a conductive lead module includes a conductor or conductive layer 950 that is positioned at the outer boundary of the electromagnetic interference immune defibrillation lead. The conductor or conductive layer 950 is insulated by insulating material 960.

Figure 12:
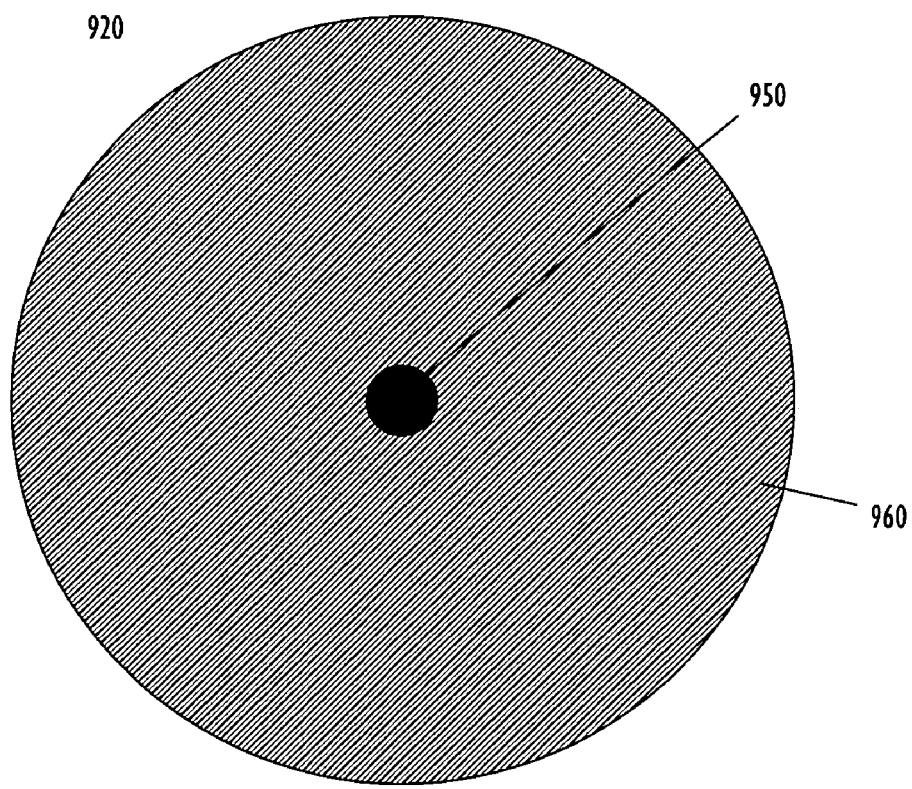
FIG. 12 illustrates a connection configuration for another end of the modular electromagnetic interference immune defibrillation lead structure, as illustrated in FIG. 10, according to the concepts of the present invention.

At the other end 920 of a conductive lead module 900, the conductor or conductive layer 950 is positioned at a center portion of the electromagnetic interference immune defibrillation lead. The positioning of the conductor or conductive layer 950 at a center portion of the electromagnetic interference immune defibrillation lead allows the end 920 of a conductive lead module 900 to connect properly with the appropriate end of capacitor module 1000. FIG. 12 provides a cross-section view of end 920 of the conductive lead module 900.

As illustrated in FIG. 12, the end 920 of a conductive lead module includes a conductor or conductive layer 950 that is positioned at the center portion of the electromagnetic interference immune defibrillation lead. The conductor or conductive layer 950 is insulated by insulating material 960.

In FIG. 10, the capacitor module 1000 includes a capacitor formed by a dielectric material 1200 sandwiched by a pair of conductors or conductive layers (1050 and 1100). The dielectric material 1200 may be a self-healing dielectric material such as cellulose triacetate, a cyanoresin, or layered aluminum oxide.

Figure 13:
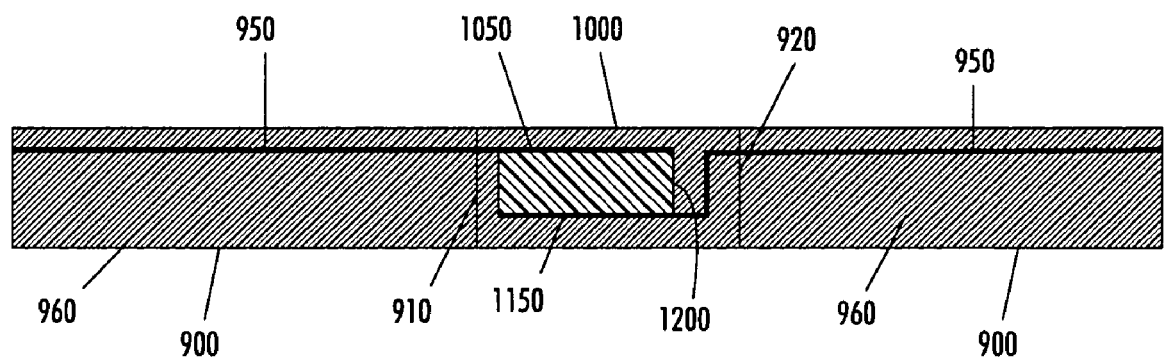
FIG. 13 illustrates another embodiment of a modular electromagnetic interference immune defibrillation lead structure according to the concepts of the present invention.

As illustrated in FIG. 13, an electromagnetic interference immune defibrillation lead can be modularly constructed. In this embodiment, an electromagnetic interference immune defibrillation lead includes a plurality of conductive lead modules 900 connected together by a capacitor module 1000. Each conductive lead module 900 includes a conductor or conductive layer 950 that is insulated by insulating material 960.

At one end 910 of a conductive lead module 900, the conductor or conductive layer 950 is positioned at an outer boundary of the electromagnetic interference immune defibrillation lead. The positioning of the conductor or conductive layer 950 at an outer boundary of the electromagnetic interference immune defibrillation lead allows the end 910 of the conductive lead module 900 to connect properly with the appropriate end of capacitor module 1000. FIG. 11 provides a cross-section view of end 910 of the conductive lead module 900.

At the other end 925 of a conductive lead module 900, the conductor or conductive layer 950 is also positioned at an outer boundary of the electromagnetic interference immune defibrillation lead. The positioning of the conductor or conductive layer 950 at the outer boundary of the electromagnetic interference immune defibrillation lead allows the end 925 of a conductive lead module 900 to connect properly with the appropriate end of capacitor module 1000.

In FIG. 13, the capacitor module 3000 includes a capacitor formed by a dielectric material 1200 sandwiched by a pair of conductors or conductive layers (1050 and 1150). In this embodiment, conductor or conductive layer 1150 is formed within the capacitor module 3000 to that positioned on an opposite side of dielectric material 1200 from conductor or conductive layer 1050. The dielectric material 1200 may be a self-healing dielectric material such as cellulose triacetate, a cyanoresin, or layered aluminum oxide.

As illustrated in FIG. 13, an electromagnetic interference immune defibrillation lead can be modularly constructed. In this embodiment, an electromagnetic interference immune defibrillation lead includes a plurality of conductive lead modules 900 connected together by a capacitor module 1000. Each conductive lead module 900 includes a conductor or conductive layer 950 that is insulated by insulating material 960.

At one end 910 of a conductive lead module 900, the conductor or conductive layer 950 is positioned at an outer boundary of the electromagnetic interference immune defibrillation lead. The positioning of the conductor or conductive layer 950 at an outer boundary of the electromagnetic interference immune defibrillation lead allows the end 910 of the conductive lead module 900 to connect properly with the appropriate end of capacitor module 1000. FIG. 11 provides a cross-section view of end 910 of the conductive lead module 900.

At the other end 925 of a conductive lead module 900, the conductor or conductive layer 950 is also positioned at an outer boundary of the electromagnetic interference immune defibrillation lead. The positioning of the conductor or conductive layer 950 at the outer boundary of the electromagnetic interference immune defibrillation lead allows the end 925 of a conductive lead module 900 to connect properly with the appropriate end of capacitor module 1000.

In FIG. 13, the capacitor module 3000 includes a capacitor formed by a dielectric material 1200 sandwiched by a pair of conductors or conductive layers (1050 and 1150). In this embodiment, conductor or conductive layer 1150 is formed within the capacitor module 3000 to that positioned on an opposite side of dielectric material 1200 from conductor or conductive layer 1050. The dielectric material 1200 may be a self-healing dielectric material such as cellulose triacetate, a cyanoresin, or layered aluminum oxide.

Figure 14:
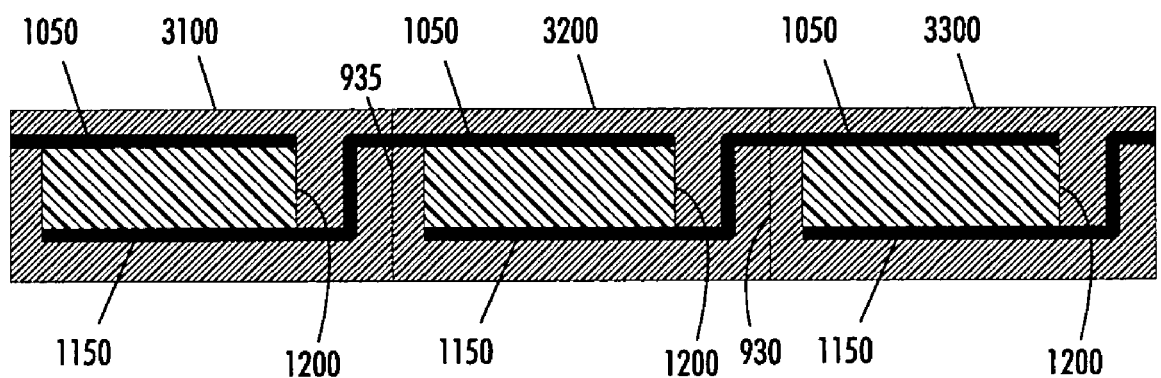
FIG. 14 illustrates another embodiment of a modular electromagnetic interference immune defibrillation lead structure according to the concepts of the present invention.

As illustrated in FIG. 14, an electromagnetic interference immune defibrillation lead can be modularly constructed. In this embodiment, an electromagnetic interference immune defibrillation lead includes a plurality of capacitor modules (3100, 3200, and 3300).

Each capacitor module (3100, 3200, and 3300) includes a capacitor formed by a dielectric material 1200 sandwiched by a pair of conductors or conductive layers (1050 and 1150). The capacitors of the various capacitor modules (3100, 3200, and 3300) are connected together serially.

In this embodiment, conductor or conductive layer 1150 is formed within the capacitor module 3000 to that positioned on an opposite side of dielectric material 1200 from conductor or conductive layer 1050. The dielectric material 1200 may be a self-healing dielectric material such as cellulose triacetate, a cyanoresin, or layered aluminum oxide.

At one end 935 of a capacitor module (3100, 3200, or 3300), the conductor or conductive layer 1050 is positioned at an outer boundary of the electromagnetic interference immune defibrillation lead. The positioning of the conductor or conductive layer 1050 at an outer boundary of the electromagnetic interference immune defibrillation lead allows the end 935 of a capacitor module (3100, 3200, or 3300) to connect properly with the appropriate end 930 of an adjacent capacitor module (3100, 3200, or 3300).

Figure 15:
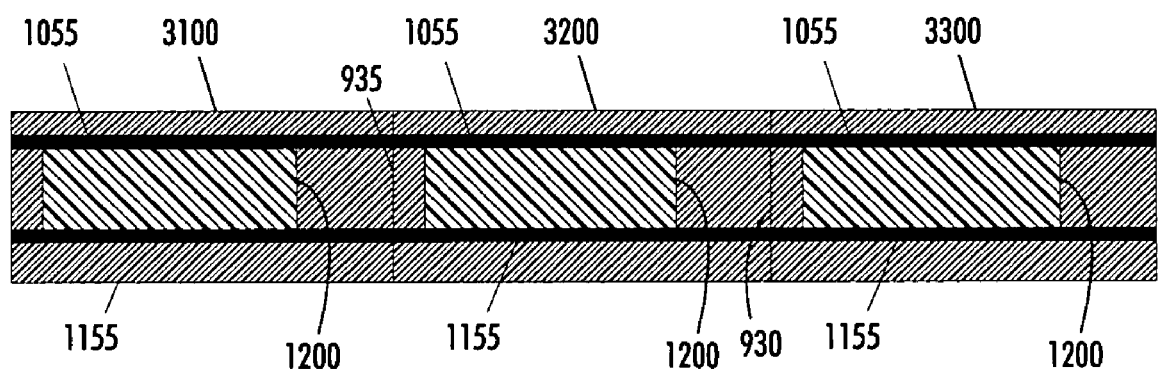
FIG. 15 illustrates another embodiment of a modular electromagnetic interference immune defibrillation lead structure according to the concepts of the present invention.

As illustrated in FIG. 15, an electromagnetic interference immune defibrillation lead can be modularly constructed. In this embodiment, an electromagnetic interference immune defibrillation lead includes a plurality of capacitor modules (3100, 3200, and 3300).

Each capacitor module (3100, 3200, and 3300) includes a capacitor formed by a dielectric material 1200 sandwiched by a pair of conductors or conductive layers (1055 and 1155). The capacitors of the various capacitor modules (3100, 3200, and 3300) are connected together in parallel.

In this embodiment, conductor or conductive layer 1155 is formed within the capacitor module 3000 to that positioned on an opposite side of dielectric material 1200 from conductor or conductive layer 1055. The dielectric material 1200 may be a self-healing dielectric material such as cellulose triacetate, a cyanoresin, or layered aluminum oxide.

At one end 935 of a capacitor module (3100, 3200, or 3300), the conductor or conductive layer 1055 is positioned at an outer boundary of the electromagnetic interference immune defibrillation lead. The positioning of the conductor or conductive layer 1055 at an outer boundary of the electromagnetic interference immune defibrillation lead allows the end 935 of a capacitor module (3100, 3200, or 3300) to connect properly with the appropriate end 930 of an adjacent capacitor module (3100, 3200, or 3300).

Figure 16:
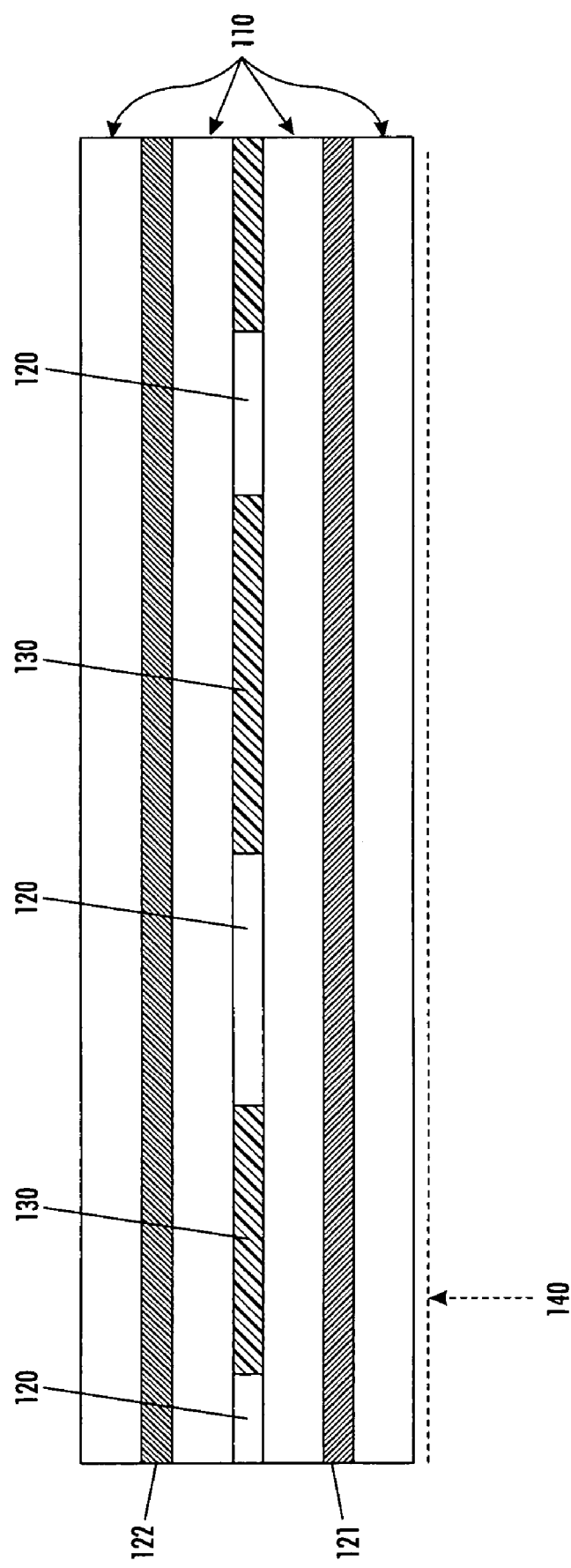
FIG. 16 illustrates another embodiment of an electromagnetic interference immune pacing/defibrillation lead according to the concepts of the present invention.

In FIG. 16, an electromagnetic interference immune pacing/defibrillation lead is illustrated. More specifically, FIG. 16 illustrates a cross-section that shows an electromagnetic interference immune defibrillation lead having layers of self-healing dielectric material 110, patches of electrically conductive material 130 with patches of insulating material 120 therebetween, a pair of electrically conductive layers or conductors (121 and 122), and a pacing wire 140.

The electrically conductive material 130 acts as a block for external electromagnetic interference. When electromagnetic interference induces a charge between the pair of electrically conductive layers or conductors (121 and 122), the dielectric material 110 prevents a current from arcing between the pair of electrically conductive layers or conductors (121 and 122) because the voltage level of the current is less than the dielectric threshold of the material.

Conversely, when an intermittent burst of current flows along the defibrillation lead having layers of self-healing dielectric material 110 and patches of electrically conductive material 130, the voltage of that current is not significantly impeded because the voltage level of that current is such that a partial dielectric breakdown occurs in the dielectric material. When the intermittent burst of current is finished, the dielectric material rapidly self-heals and resumes its role in shielding the wire.

In a preferred embodiment, the self-healing dielectric material is cellulose triacetate and the electrically conductive material is copper. It is noted that other self-healing dielectric materials can be used in the present invention, such as aluminum oxide ($Al_2O_3$).

It is noted that the defibrillation lead of FIG. 16 is a plurality of parallel serially connected capacitor pairs. A serially connected capacitor pair is formed by self-healing dielectric material 110 between a patch of conductive material 130 and the pair of electrically conductive layers or conductors (121 and 122), as illustrated in FIG. 17.

By connecting the serially connected capacitor pairs in parallel, the capacitance of each capacitor pair will add together. The use of a parallel circuit of capacitor pairs increases the total storage of electric charge. However, the total voltage rating of the capacitors does not change. Every capacitor will "see" the same voltage. Thus, it is preferred that all the capacitor pairs be rated for the same voltage because the capacitor pair with lowest voltage rating will govern the breakdown.

Figure 17:
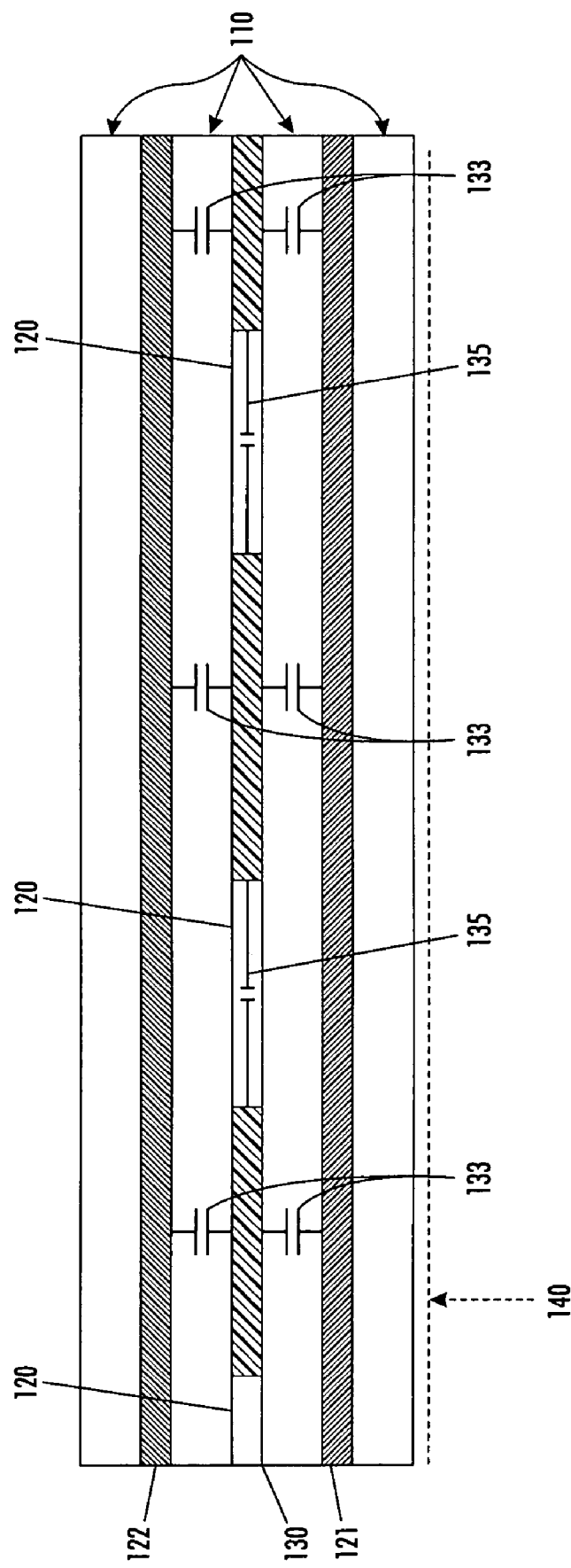
FIG. 17 illustrates a circuit equivalent of the electromagnetic interference immune defibrillation lead of FIG. 16.

As illustrated in FIG. 17, the structure; formed by a patch of conductive material 130, the self-healing dielectric material 110, and the pair of electrically conductive layers or conductors (121 and 122); creates a capacitance, thereby forming non-coplanar capacitors 133 or a capacitor pair. Moreover, the structure, formed by adjacent coplanar patches of conductive material 130 and the patch of insulating material 120 therebetween, creates a capacitance, thereby forming a circuit equivalent coplanar capacitor 135.

The insulating material 120 may be chosen for certain dielectric properties in accordance with the desired breakdown properties between adjacent coplanar patches of conductive material 130. Thus, by changing dielectric properties of the insulating material 120, the overall capacitance of the electromagnetic interference immune defibrillation lead can be varied. Moreover, it is noted that the insulating material 120 may also be composed of a self-healing dielectric material such as cellulose triacetate, a cyanoresin, or layered aluminum oxide.

In the above description of FIG. 17, coplanar refers to conductive patches being formed in a same layer or substrate or part of a common wrap or tape, and non-coplanar refers to conductive patches being formed in different layers or substrates or part of different wraps or tapes.

Figure 18:
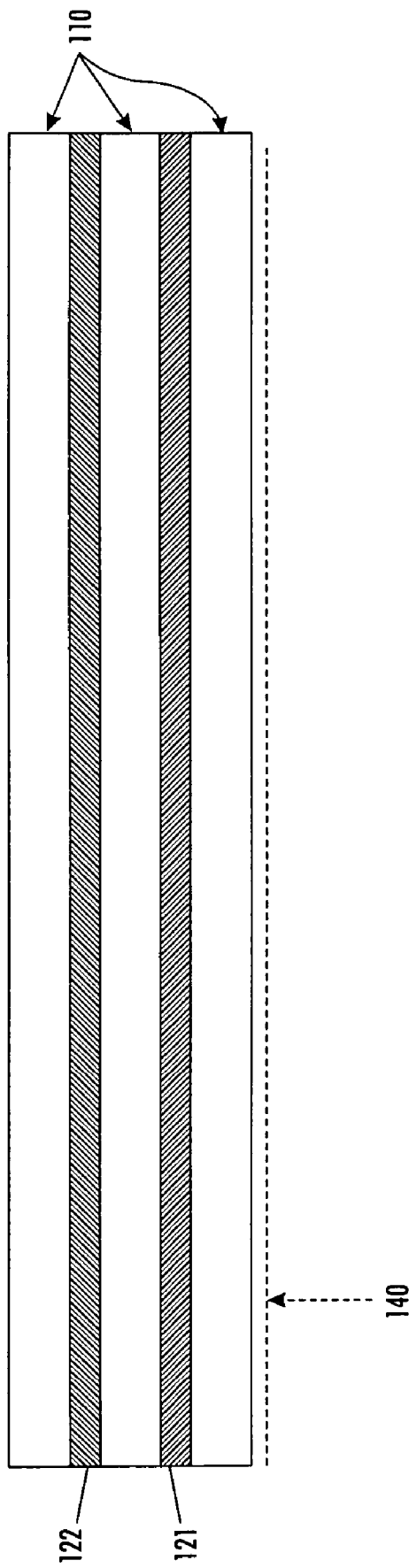
FIG. 18 illustrates another embodiment of an electromagnetic interference immune pacing/defibrillation lead according to the concepts of the present invention.

In FIG. 18, an electromagnetic interference immune pacing/defibrillation lead is illustrated. More specifically, FIG. 18 illustrates a cross-section that shows an electromagnetic interference immune defibrillation lead having a layer of self-healing dielectric material 110 between a pair of electrically conductive layers or conductors (121 and 122) and a pacing wire 140. A proximal end of one of the electrically conductive layers or conductors (121 and 122) is connected to an energy or voltage source (not shown) and the distal end of the electrically conductive layer or conductor (121 or 122), not connected to the energy or voltage source, is connected to an electrode (not shown) for applying the voltage to the heart tissue. The distal end of the electrically conductive layer or conductor (121 or 122) connected to the energy or voltage source is electrically insulated. The proximal end of the electrically conductive layer or conductor (121 or 122) connected to the electrode is electrically insulated. Thus, to complete the electrical path, the electrical energy must arc through the layer of self-healing dielectric material 110 between a pair of electrically conductive layers or conductors (121 and 122).

When electromagnetic interference induces a charge between the pair of electrically conductive layers or conductors (121 and 122), the dielectric material 110 prevents a current from arcing between the pair of electrically conductive layers or conductors (121 and 122) because the voltage level of the current is less than the dielectric threshold of the material.

Conversely, when an intermittent burst of current flows along the defibrillation lead having a layer of self-healing dielectric material 110 between a pair of electrically conductive layers or conductors (121 and 122), the voltage of that current is not significantly impeded because the voltage level of that current is such that a partial dielectric breakdown occurs in the dielectric material. When the intermittent burst of current is finished, the dielectric material rapidly self-heals and resumes its role in shielding the wire.

In a preferred embodiment, the self-healing dielectric material is cellulose triacetate and the electrically conductive material is copper. It is noted that other self-healing dielectric materials can be used in the present invention, such as aluminum oxide ($Al_2O_3$).

It is noted that the defibrillation lead of FIG. 18 is a single capacitor that traverses substantially the entire length of the defibrillation lead. The capacitor 133 is formed by self-healing dielectric material 110 between the pair of electrically conductive layers or conductors (121 and 122), as illustrated in FIG. 19.

Figure 19:
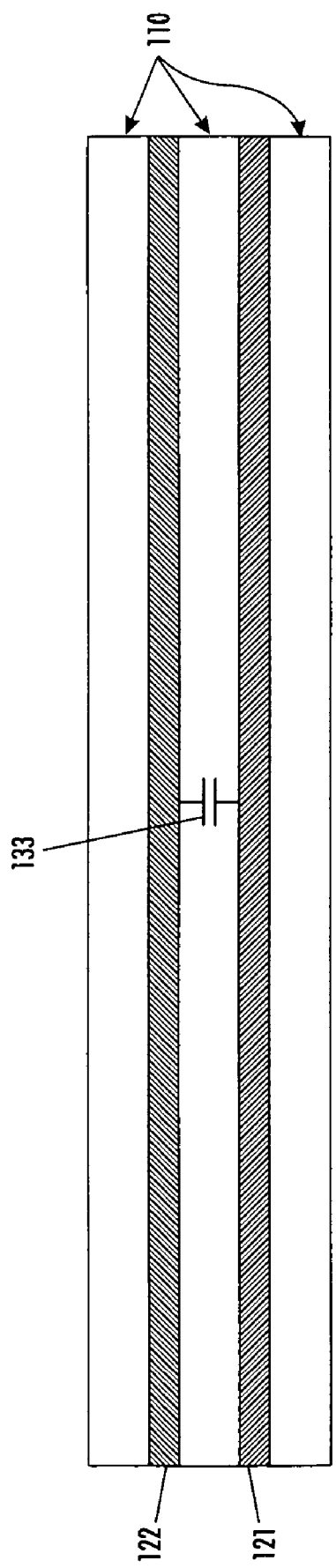
FIG. 19 illustrates a circuit equivalent of the electromagnetic interference immune defibrillation lead of FIG. 18.

As illustrated in FIG. 19, the structure, formed by the self-healing dielectric material 110 and the pair of electrically conductive layers or conductors (121 and 122), creates a capacitance, thereby forming a capacitor 133.

As noted above, the present invention is directed to an electromagnetic interference immune pacing/defibrillation lead. The device includes a pacing lead; a first electromagnetic insulating layer formed around the pacing lead; a first layer formed on the first electromagnetic insulating layer, the first layer having a plurality of first conductive rings composed of first conductive material, each first conductive ring being separated by first insulating material; a second electromagnetic insulating layer formed on the first layer; a second layer formed on the second electromagnetic insulating layer, the second layer having a plurality of second conductive rings composed of second conductive material, each second conductive ring being separated by second insulating material; and a third electromagnetic insulating layer formed on the second layer.

The second conductive rings of second conductive material are positioned such that a second conductive ring overlaps a portion of a first conductive ring and overlaps a portion of an adjacent first conductive ring. The overlapping relationship between the conductive rings of the first layer and the conductive rings of second layer creating a circuit of a plurality of serially connected capacitors.

The first, second, and third electromagnetically insulating layers may be composed of a self-healing dielectric material such as cellulose triacetate, a cyanoresin, or layered aluminum oxide. The first and second insulating materials may be a self-healing dielectric material such as cellulose triacetate, a cyanoresin, or layered aluminum oxide.

The dielectric material has a threshold greater than voltage induced by magnetic resonance imaging or an undesired electromagnetic interference and less than voltage needed to initiate a breakdown of the dielectric material and cause a defibrillation signal to be effectively conducted.

The second layer may have a spiraling coil of loops, the spiraling coil being composed of second conductive material, each loop being separated by second insulating material. The spiraling coil of loops is positioned such that a section of the spiraling coil of loops ring overlaps a portion of a first conductive ring and overlaps a portion of an adjacent first conductive ring.

The electromagnetic interference immune defibrillation lead includes a first electromagnetic insulating layer; a first layer, formed on the first electromagnetic insulating layer, the first layer having a plurality of first conductive rings composed of first conductive material, each first conductive ring being separated by first insulating material; a second electromagnetic insulating layer formed on the first layer; a second layer, formed on the second electromagnetic insulating layer, the second layer having a plurality of second conductive rings composed of second conductive material, each second conductive ring being separated by second insulating material; and a third electromagnetic insulating layer formed on the second layer.

The second conductive rings of second conductive material are positioned such that a second conductive ring overlaps a portion of a first conductive ring and overlaps a portion of an adjacent first conductive ring. The overlapping relationship between the conductive rings of the first layer and the conductive rings of second layer creating a circuit of a plurality of serially connected capacitors.

The first, second, and third electromagnetically insulating layers may be composed of a self-healing dielectric material such as cellulose triacetate, a cyanoresin, or layered aluminum oxide. The first and second insulating materials may be a self-healing dielectric material such as cellulose triacetate, a cyanoresin, or layered aluminum oxide.

The dielectric material has a threshold greater than voltage induced by magnetic resonance imaging or an undesired electromagnetic interference and less than voltage needed to initiate a breakdown of the dielectric material and cause a defibrillation signal to be effectively conducted.

The second layer may have a spiraling coil of loops, the spiraling coil being composed of second conductive material, each loop being separated by second insulating material. The spiraling coil of loops is positioned such that a section of the spiraling coil of loops ring overlaps a portion of a first conductive ring and overlaps a portion of an adjacent first conductive ring.

The electromagnetic interference immune defibrillation lead may be formed by providing a first electromagnetic insulating layer; forming metalized strips on the first electromagnetic insulating layer; providing a second electromagnetic insulating layer; forming metalized strips on the second electromagnetic insulating layer; providing a third electromagnetic insulating layer; and fusing the first, second, and third electromagnetic insulating layers together such that the metalized strips on the first electromagnetic insulating layer contact the third electromagnetic insulating layer and the metalized strips on the second electromagnetic insulating layer contact the third electromagnetic insulating layer. The method may also roll the fused first, second, and third electromagnetic insulating layers to form a sleeve.

The metalized strips on the first electromagnetic insulating layer may be positioned such that a metalized strip on the first electromagnetic insulating layer overlaps a portion of a first metalized strip on the second electromagnetic insulating layer and overlaps a portion of an adjacent metalized strip on the second electromagnetic insulating layer. The overlapping relationship between the metalized strips of the first electromagnetic insulating layer and the metalized strips of second electromagnetic insulating layer creating a circuit of a plurality of serially connected capacitors.

The first, second, and third electromagnetically insulating layers may be composed of a self-healing dielectric material such as cellulose triacetate, a cyanoresin, or layered aluminum oxide. The dielectric material has a threshold greater than voltage induced by magnetic resonance imaging or an undesired electromagnetic interference and less than voltage needed to initiate a breakdown of the dielectric material and cause a defibrillation signal to be effectively conducted.

An electromagnetic interference immune pacing/defibrillation lead may be formed by providing a pacing lead; wrapping a first tape, spirally, around the pacing lead, the first tape being composed of a first insulating substrate with conductive strips formed thereon, the first tape being wrapped such that the first insulating substrate is adjacent the pacing lead, the conductive strips being formed at an angle on the first insulating substrate such that upon wrapping the conductive strips form conductive rings that conduct circumferentially; wrapping a second tape, spirally, around the first tape, the second tape being composed of a second insulating substrate; and wrapping a third tape, spirally, around the second tape, the third tape being composed of a third insulating substrate with conductive strips formed thereon, the third tape being wrapped such that the conductive strips are adjacent the second tape, the conductive strips being formed at an angle on the third insulating substrate such that upon wrapping the conductive strips form conductive rings that conduct circumferentially.

The third tape may be wrapped such that a conductive ring of the third tape overlaps a portion of a first conductive ring of the first tape and overlaps a portion of a second conductive ring of the first tape, the second conductive ring of the first tape being adjacent to the first conductive ring of the first tape. The overlapping relationship between the conductive rings of the first tape and the conductive rings of second tape creating a circuit of a plurality of serially connected capacitors.

The first, second, and third insulating substrates may be composed of a self-healing dielectric material such as cellulose triacetate, a cyanoresin, or layered aluminum oxide. The dielectric material has a threshold greater than voltage induced by magnetic resonance imaging or an undesired electromagnetic interference and less than voltage needed to initiate a breakdown of the dielectric material and cause a defibrillation signal to be effectively conducted.

While various examples and embodiments of the present invention have been shown and described, it will be appreciated by those skilled in the art that the spirit and scope of the present invention are not limited to the specific description and drawings herein, but extend to various modifications and changes.

What is claimed is:

1. An electromagnetic interference immune implantable medical device, comprising:
   a selectively conductive structure;
   said selectively conductive structure including:
   a first electromagnetic insulating layer;
   a first layer, formed on said first electromagnetic insulating layer, said first layer having a plurality of first conductive rings each having a first width and length and being composed of first conductive material, each first conductive ring being separated by a first insulating material, a second electromagnetic insulating layer having said first length and a second narrower width than said first width;
   a second electromagnetic insulating layer formed on said first layer;
   a second layer, formed on said second electromagnetic insulating layer, said second layer having a plurality of second conductive rings forming a continuous spiraling coil of loops, each loop having said first width and length, said plurality of second conductive rings being composed of second conductive material, and wherein each loop of said continuous spiraling coil of loops is separated by a second insulating material having said first length and said second narrower width; and
   a third electromagnetic insulating later formed on said second layer;
   wherein said plurality of first conductive rings are regularly spaced with respect to said first insulating material, and wherein said continuous spiraling coil of loops formed by said plurality of second conductive rings is positioned such that each loop of said continuous spiraling coil of loops overlaps a portion of a conductive ring of said first conductive rings and overlaps a portion of an adjacent conductive ring of said first conductive rings; and
   wherein at least one of said first, second, and third electromagnetically insulating layers comprises a self-heating dielectric material.

2. The electromagnetic interference immune implantable medical device as claimed in claim 1, wherein at least one of said first, second, and third electromagnetically insulating layers is composed of cellulose triacetate.

3. The electromagnetic interference immune implantable medical device as claimed in claim 1, wherein said dielectric material has a threshold greater than voltage induced by magnetic resonance imaging and less than voltage needed to initiate a breakdown of said dielectric material, to cause a defibrillation signal to be effectively conducted.

4. The electromagnetic interference immune implantable medical device as claimed in claim 1, wherein said dielectric material has a threshold greater than voltage induced by undesired electromagnetic interference and less than voltage needed to initiate a breakdown of said dielectric material, to cause a defibrillation signal to be effectively conducted.

5. The electromagnetic interference immune implantable medical device as claimed in claim 1, further comprising:
   a sensing lead;
   said first electromagnetic insulating layer formed around said sensing lead.

6. The electromagnetic interference immune implantable medical device as claimed in claim 1, wherein said second electromagnetically insulating layer has a threshold greater than voltage induced by magnetic resonance imaging and less than voltage needed to initiate a breakdown of said second electromagnetically insulating layer and cause a defibrillation signal to be effectively conducted.

7. The electromagnetic interference immune implantable medical device as claimed in claim 1, wherein said second electromagnetically insulating layer has a threshold greater than voltage induced by undesired electromagnetic interference and less than voltage needed to initiate a breakdown of said second electromagnetically insulating layer and cause a defibrillation signal to be effectively conducted.

8. The electromagnetic interference immune implantable medical device as claimed in claim 1, wherein at least two of said first, second, and third electromagnetically insulating layers is composed of a self-healing dielectric material.

9. The electromagnetic interference immune implantable medical device as claimed in claim 1, wherein said first, second, and third electromagnetically insulating layers are composed of a self-healing dielectric material.

10. The electromagnetic interference immune implantable medical device as claimed in claim 1, wherein said second conductive rings are regularly spaced with respect to said second insulating material.

* * * * *